United States Patent [19]
Bohme et al.

[11] Patent Number: 6,150,387
[45] Date of Patent: Nov. 21, 2000

[54] HETEROCYCLIC CARBOXAMIDE COMPOUNDS EFFECTIVE IN THE TREATMENT OF DRUG ABUSE

[75] Inventors: Andrees Bohme, Paris; Marie-Christine Dubroeucq, Enghein-les-Bains, both of France; Walter Fratta, Cagliari, Italy; Claude Guyon, Saint-Maur-des-Fosses, France; Assunta Imperato, Paris, France; Franco Manfre, Limeil-Brevannes, France

[73] Assignee: Rhone-Poulenc Rorer S.A., Antony, France

[21] Appl. No.: 09/117,931

[22] PCT Filed: Feb. 3, 1997

[86] PCT No.: PCT/FR97/00209

§ 371 Date: Aug. 7, 1998

§ 102(e) Date: Aug. 7, 1998

[87] PCT Pub. No.: WO97/28798

PCT Pub. Date: Aug. 14, 1997

[30] Foreign Application Priority Data

Feb. 7, 1996 [FR] France ................................. 96/01481

[51] Int. Cl.$^7$ ..................... A61K 31/425; A61K 31/47; A61K 31/44; A61K 31/40
[52] U.S. Cl. ........................ 514/365; 514/314; 514/340; 514/369; 514/423
[58] Field of Search ................................... 514/365, 314, 514/340, 369, 423

[56] References Cited

U.S. PATENT DOCUMENTS

| | | |
|---|---|---|
| 5,610,144 | 3/1997 | Capet et al. |
| 5,624,939 | 4/1997 | Capet et al. ............................. 514/314 |
| 5,633,270 | 5/1997 | Dubroeucq et al. .................... 514/365 |
| 5,637,602 | 6/1997 | Capet et al. ............................. 514/365 |

FOREIGN PATENT DOCUMENTS

| | | |
|---|---|---|
| WO 93/01167 | 1/1993 | WIPO. |
| WO 93/12791 | 7/1993 | WIPO. |
| WO 94/15914 | 7/1994 | WIPO. |
| WO 94/15954 | 7/1994 | WIPO. |
| WO 94/15955 | 7/1994 | WIPO. |
| WO 96/38139 | 12/1996 | WIPO. |

OTHER PUBLICATIONS

Derwent Abstract of WO 94/15954, 1994.
Derwent Abstract of WO 93/01167, 1993.
Derwent Abstract of WO 94/15955, 1994.
Derwent Abstract of WO 94/15914, 1994.
Derwent Abstract of WO 96/38139, 1996.
Lakhbir Singh et al., "Modulation of the in vivo actions of morphine by the mixed $CCK_{A/B}$ receptor antagonist PD 142898," *European Journal of Pharmacology*, vol. 307, No. 3, 1996, pp. 283–289.
Bill W. Massey et al., "Effects of cholecystokinin antagonists on the discriminative stimulus effects of cocaine in rats and monkeys," *Drug and Alcohol Dependence*, vol. 34, No. 2, 1994, pp. 105–111.
J. Hughes et al., "Neuropeptides," *Arzneimittel–Forschung Drug Research*, vol. 42 (I), No. 2a, 1992, pp. 250–255.
A. Kuzmin et al., "Calcium Antagonists Isradipine and Nimodipine Suppress Cocaine and Morphine Intravenous Self–Administration in Drug–Naive Mice," *Pharmacology Biochemistry and Behavior*, vol. 41, 1992, pp. 497–500.

*Primary Examiner*—William R. A. Jarvis
*Attorney, Agent, or Firm*—Finnegan, Henderson, Farabow, Garrett & Dunner, L.L.P.

[57] ABSTRACT

This invention relates to the use of heterocyclic carboxamide compounds for preventing or reducing self-administration, by a human or animal patient, of a drug or a substance capable of giving rise to pharmacomania or to overuse. The preferred types of drugs or substances are nicotine, caffeine, benzodiazepines, narcotics, and hallucinogens.

12 Claims, No Drawings

HETEROCYCLIC CARBOXAMIDE COMPOUNDS EFFECTIVE IN THE TREATMENT OF DRUG ABUSE

This application is a 371 of PCT/FR97/00209, filed Feb. 3, 1997.

Today, drug dependence, pharmacomania and, more generally, the abuse of legal or banned substances is a major problem in the world, and products enabling these behaviour patterns to be decreased or abolished have become necessary.

Compounds enabling drug abuse or the abuse of substances giving rise to pharmacomania or to overuse, that is to say compounds which decrease or abolish the taking of these products, have now been found, and this forms the subject of the present application. Among these drugs and substances giving rise to pharmacomania or to overuse, there may be mentioned nicotine, benzodiazepines, caffeine, narcotics such as amphetamines, cocaine, cannabinoids, morphine and derivatives and opioids, hallucinogens such as LSD, ecstasy, mescaline and psylocibin and, in general, all compounds whose abuse poses a public health problem.

The present invention relates to the use of derivatives of formula:

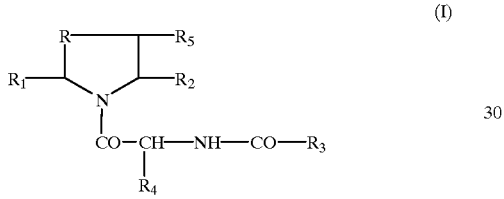

(I)

their racemates and enantiomers when they contain one or more asymmetric centres and their salts, for the treatment of drug abuse or the abuse of substances giving rise to pharmacomania or to overuse, with the exception of alcohol abuse.

The present invention also relates to the use of these compounds for the manufacture of a medicament intended for the treatment of drug abuse or the abuse of substances giving rise to pharmacomania or to overuse, with the exception of alcohol abuse.

In the formula (I), either R represents a methylene, ethylene, SO, $SO_2$ or CHOH radical or a sulphur atom, $R_1$ represents a pyridyl radical optionally substituted with one or more alkyl radicals, a furyl radical optionally substituted with one or more alkyl radicals, a thienyl radical optionally substituted with one or more alkyl radicals, a quinolyl radical optionally substituted with one or more alkyl radicals, a naphthyl radical optionally substituted with one or more alkyl radicals, an indolyl radical optionally substituted with one or more alkyl radicals or a phenyl radical optionally substituted with one or more substituents chosen from halogen atoms and alkyl, alkoxy, hydroxyl, nitro, amino, monoalkylamino, dialkylamino, alkoxycarbonyl, —CO—$NR_7R_8$—NH—CO—$CH_3$, trifluoromethyl and trifluoromethoxy radicals and $R_5$ represents a hydrogen atom, or R represents a methylene radical, $R_1$ represents a hydrogen atom and $R_5$ represents a phenyl radical, or R represents a $CHR_6$ radical and $R_1$ and $R_5$ each represent a hydrogen atom, $R_2$ represents an alkoxycarbonyl, cycloalkyloxycarbonyl, cycloalkylalkyloxycarbonyl or —$CONR_9R_{10}$ radical or a phenyl radical optionally substituted with one or more substituents chosen from alkyl, alkoxy and hydroxyl radicals, $R_3$ represents a phenyl (optionally substituted with one or more substituents chosen from halogen atoms and alkyl, alkoxy and alkylthio radicals), naphthyl, indolyl or quinolyl radical or a phenylamino radical in which the phenyl ring is optionally substituted with one or more substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O -alk-COOX, —CH═CH—COOX and —CO—COOX radicals, -alk-$SO_3H$ radicals in salt form and —CH═CH-alk', —C(═NOH)—COOX, —S-alk-COOX, —O—$CH_2$-alk'-COOX, —CX═N—O-alk-COOX, -alk-N(OH)—CO-alk and 2,2-dimethyl-4,6-dioxo-1,3-dioxan-5-yl radicals, $R_4$ represents a hydrogen atom or an alkyl radical, $R_6$ represents a phenyl radical, $R_7$ represents a hydrogen atom or an alkyl or phenylalkyl radical or a phenyl radical optionally substituted with one or more substituents chosen from halogen atoms and alkyl, alkoxy and alkylthio radicals, $R_8$ represents an alkyl or phenylalkyl radical or a phenyl radical optionally substituted with one or more substituents chosen from halogen atoms and alkyl, alkoxy and alkylthio radicals, or alternatively $R_7$ and $R_8$, with the nitrogen atom to which they are attached, form a saturated or unsaturated, mono- or polycyclic heterocycle containing 4 to 9 carbon atoms and one or more hetero atoms (O, N) and optionally substituted with one or more alkyl radicals, $R_9$ represents a hydrogen atom or an alkyl, cycloalkylalkyl, cycloalkyl or phenylalkyl radical or a phenyl radical optionally substituted with one or more substituents chosen from halogen atoms and alkyl, alkoxy and alkylthio radicals, $R_{10}$ represents an alkyl, cycloalkylalkyl, cycloalkyl or phenylalkyl radical or a phenyl radical optionally substituted with one or more substituents chosen from halogen atoms and alkyl, alkoxy and alkylthio radicals, or alternatively $R_9$ and $R_{10}$, together with the nitrogen atom to which they are attached, form a saturated or unsaturated, mono- or polycyclic heterocycle containing 4 to 9 carbon atoms and one or more hetero atoms (O, N, S) and optionally substituted with one or more alkyl radicals, X represents a hydrogen atom or an alkyl or phenylalkyl radical, alk represents an alkyl or alkylene radical, alk' represents a hydroxyalkyl, hydroxyalkylene, alkoxyalkyl or alkoxyalkylene radical.

In the foregoing definitions and those which will be mentioned below, except where otherwise stated, the alkyl, alkylene and alkoxy radicals and alkyl, alkylene and alkoxy portions contain 1 to 4 carbon atoms in an unbranched or branched chain, the acyl radicals or portions contain 2 to 4 carbon atoms and the cycloalkyl radicals and portions contain 3 to 6 carbon atoms.

When $R_7$ and $R_8$, with the nitrogen atom to which they are attached, form a heterocycle, the latter is preferably a piperidino ring optionally substituted with one or more alkyl radicals or a 1,2,3,4-tetrahydroquinoline ring system.

When $R_9$ and $R_{10}$, with the nitrogen atom to which they are attached, form a heterocycle, the latter is preferably a piperidino, perhydro-1-azepinyl, 1,2,3,6-tetrahydro-1-pyridyl, 1,2,3,4-tetrahydro-1-quinolyl, 1-pyrrolidinyl, 1,2,3,4-tetrahydro-2-isoquinolyl, thiomorpholino or 1-indolyl ring system, it being possible for these ring systems to be optionally substituted with at least one alkyl radical.

The compounds of formula (I) containing one or more asymmetric centres possess isomeric forms. The racemates and the enantiomers of these compounds also form part of the invention.

The compounds of formula (I) can, where appropriate, exist in the form of addition salts with an inorganic or organic acid.

The compounds of formula (I) containing a carboxyl, sulpho or alk-$SO_3H$ residue can also exist in the form of pharmaceutically acceptable metal salts or addition salts with nitrogenous bases.

As examples of pharmaceutically acceptable salts, there may be mentioned the addition salts with inorganic or organic acids (such as acetate, propionate, succinate, benzoate, fumarate, maleate, oxalate, methanesulphonate, isethionate, theophyllineacetate, salicylate, methylenebis(β-hydroxynaphthoate), hydrochloride, sulphate, nitrate and phosphate), the salts with alkali metals (sodium, potassium, lithium) or with alkaline-earth metals (calcium, magnesium), the ammonium salt and the salts of nitrogenous bases (ethanolamine, trimethylamine, methylamine, benzylamine, N-benzyl-β-phenethylamine, choline, arginine, leucine, lysine, N-methylglucamine).

The compounds of formula (I) and their salts may be prepared under the conditions described in International Application WO 93/01167.

According to International Application WO 93/01167, the compounds of formula (I) display advantageous pharmacological properties. These compounds possess a strong affinity for cholecystokinin (CCK) and gastrin receptors, and are hence useful in the treatment and prevention of disorders associated with CCK and with gastrin in relation to the nervous system and the gastrointestinal system.

Thus, according to International Application PCT WO 93/01167, the compounds may be used for the treatment or prevention of psychoses, anxiety disorders, Parkinson's disease, tardive dyskinesia, irritable bowel syndrome, acute pancreatitis, ulcers, disorders of intestinal motility and certain CCK-sensitive tumours, and as an appetite regulator. These compounds, which also have a potentiating effect on the analgesic activity of narcotic and non-narcotic medicaments, can have an analgesic effect of their own. Moreover, compounds which have a strong affinity for CCK receptors modify the capacities for memorization and can be effective in memory disorders.

The effect of the compounds of formula (I) for the treatment of drug abuse or the abuse of substances giving rise to pharmacomania or to overuse was evaluated in the test of self-administration of drugs in mice according to the protocol described by A. Kuzmin et al., Pharmacol. Biochem. Behav., 41, 497–500 (1992) for morphine and cocaine. In this test, the compounds of formula (I) at doses equal to or less than 100 mg/kg deter the self-administration of drugs or of substances giving rise to pharmacomania or to overuse (amphetamine, cocaine, morphine, diazepam, mescaline).

Of special importance are the compounds of formula (I) for which R represents a methylene radical, a sulphur atom or an SO radical, $R_1$ represents an optionally substituted phenyl radical, $R_2$ represents a phenyl or alkoxycarbonyl radical, $R_4$ and $R_5$ represent a hydrogen atom and $R_3$ represents a phenylamino radical in which the phenyl ring is substituted with a carboxyl, alk-COOH, S-alk-COOH, hydroxyalkyl, alk'-COOH, alk-$SO_3H$ or hydroxyiminoalkyl radical, their racemates and enantiomers when they contain one or more asymmetric centres and their salts. More especially advantageous are the products of formula (I) in which $R_1$ and $R_2$ are in the cis position with respect to one another.

Of special importance are the following compounds:
tert-butyl (2RS,5SR)-1-{2-[3-(3-((RS)-1-hydroxyethyl)phenyl)ureido]acetyl}-5-phenylprolinate
2-{3-{3-[2-((2S,5R)-2-tert-butoxycarbonyl-5-phenyl-1-pyrrolidinyl)-2-oxoethyl]ureido}phenyl}propionic acid,
(2RS,5SR)-{3-{3-[2-(2-tert-butoxycarbonyl-5-phenyl-1-pyrrolidinyl)-2-oxoethyl]ureido}phenylthio}acetic acid,
(2R,4R)-3-{3-[2-(4-tert-butoxycarbonyl-2-(2-fluorophenyl)-3-thiazolidinyl)-2-oxoethyl]ureido}phenylacetic acid,
2-{3-{3-[2-((2R,4R)-4-tert-butoxycarbonyl-2-(2-fluorophenyl)-3-thiazolidinyl)-2-oxoethyl]ureido}phenyl}propionic acid,
potassium (RS)-1-{3-{3-[2-((2R,4R)-4-tert-butoxycarbonyl-2-phenyl-3-thiazolidinyl)-2-oxoethyl]ureido}phenyl}ethanesulphonate,
potassium (RS)-1-{3-{3-[2-((2S,5R)-2-tert-butoxycarbonyl-5-phenyl-1-pyrrolidinyl)-2-oxoethyl]ureido}phenyl}ethanesulphonate,
potassium (2S,5R)-1-{3-{3-[2-(2-tert-butoxycarbonyl-5-phenyl-1-pyrrolidinyl)-2-oxoethyl]ureido}phenyl}methanesulphonate,
(2S,5R)-3-{3-[2-(2-tert-butoxycarbonyl-5-phenyl-1-pyrrolidinyl)-2-oxoethyl]ureido}benzoic acid,
(2RS,5SR)-3-{3-{2-[2-tert-butoxycarbonyl-5-(2-fluorophenyl)-1-pyrrolidinyl]-2-oxoethyl}ureido}benzoic acid,
cis-3-{3-[2-(2,5-diphenyl-1-pyrrolidinyl)- 2-oxoethyl]ureido}benzoic acid,
(2RS,5SR)-3-{3-{2-[2-(2-hydroxyphenyl)-5-phenyl-1-pyrrolidinyl]-2-oxoethyl}ureido}phenylacetic acid,
(2R,4R)-3-{3-[2-(4-tert-butoxycarbonyl-2-phenyl-3-thiazolidinyl)-2-oxoethyl]ureido}phenylacetic acid,
(2R,4R)-3-{3-[2-(4-tert-butoxycarbonyl-2-phenyl-3-thiazolidinyl)-2-oxoethyl]ureido}benzoic acid,
2-{3-{3-[2-((1RS,2R,4R)-4-tert-butoxycarbonyl-2-(2-fluorophenyl)-3-thiazolidinyl 1-oxide)-2-oxoethyl]ureido}phenyl}propionic acid,
(2R,4R)-3-{3-[2-(4-tert-butoxycarbonyl-2-(2,3-difluorophenyl)-3-thiazolidinyl)-2-oxoethyl]ureido}phenylacetic acid,
tert-butyl (2RS,5SR)-1-{2-{3-[(E)-3-(1-hydroxyiminoethyl)phenyl]ureido}acetyl}-5-phenylprolinate,
their racemates and enantiomers when they contain one or more asymmetric centres and their salts.

The medicaments according to the invention consist of a compound of formula (I), in free form or in the form of a pharmaceutically acceptable addition salt with an acid, in the pure state or in the form of a composition in which it is combined with any other pharmaceutically compatible product, which may be inert or physiologically active. The medicaments according to the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also comprise substances other than diluents, for example one or more lubricants such as magnesium stearate or talc, a colouring, a coating (dragées) or a varnish.

As liquid compositions for oral administration, pharmaceutically acceptable solutions, suspensions, emulsions, syrups and elixirs may be used, containing inert diluents such as water, ethanol, glycerol, vegetable oils or liquid paraffin. These compositions can comprise substances other than diluents, for example wetting, sweetening, thickening, flavouring or stabilizing products.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting, tonicity, emulsifying, dispersing and stabilizing agents. The sterilization may be carried out in several ways, for example by aseptic filtration, by incorporation of sterilizing agents in the composition, by irradiation or by heating. They may also be manufactured in the form of sterile solid compositions which can be dissolved at the time of use in sterile water or any other sterile injectable medium.

The compositions for rectal administration are suppositories or rectal capsules which contain, besides the active product, excipients such as cocoa butter, semi-synthetic glycerides or polyethylene glycols.

The compositions for topical administration can be, for example, creams, lotions, eyewashes, mouthwashes, nasal drops or aerosols.

In human therapy, the medicaments according to the invention are especially useful in the treatment of drug abuse or the abuse of substances giving rise to pharmacomania or to overuse, with the exception of alcohol abuse.

The doses depend on the effect sought, the treatment period and the administration route used; they are generally between 0.05 g and 1 g daily via the oral route for an adult, with single doses ranging from 10 mg to 500 mg of active substance.

Generally speaking, the doctor will determine the appropriate dosage in accordance with the age, the weight and all the other factors specific to the subject to be treated.

The examples which follow illustrate some medicaments according to the invention:

EXAMPLE A

Hard gelatin capsules containing a 50 mg dose of active product and having the following composition are manufactured according to the usual technique:

Compound of formula (I) . . . 50 mg
Cellulose . . . 18 mg
Lactose . . . 55 mg
Colloidal silica . . . 1 mg
Sodium carboxymethylstarch . . . 10 mg
Talc . . . 10 mg
Magnesium stearate . . . 1 mg

EXAMPLE B

Tablets containing a 50 mg dose of active product and having the following composition are manufactured according to the usual technique:

Compound of formula (I) . . . 50 mg
Lactose . . . 104 mg
Cellulose . . . 40 mg
Povidone . . . 10 mg
Sodium carboxymethylstarch . . . 22 mg
Talc . . . 10 mg
Magnesium stearate . . . 2 mg
Colloidal silica . . . 2 mg
Mixture of hydroxymethyl-cellulose, glycerol and titanium oxide (72:3.5:24.5) q.s. 1 finished film-coated tablet weighing 245 mg

EXAMPLE C

An injection containing 10 mg of active product and having the following composition is manufactured:

Compound of formula (I) . . . 10 mg
Benzoic acid . . . 80 mg
Benzyl alcohol . . . 0.06 cm$^3$
Sodium benzoate . . . 80 mg
Ethanol, 95% . . . 0.4 cm$^3$
Sodium hydroxide . . . 24 mg
Propylene glycol . . . 1.6 cm$^3$
Water . . . q.s. 4 cm$^3$

What is claimed is:

1. A method of preventing or reducing self-administration, by a human or animal patient, of a drug or a substance capable of giving rise to pharmacomania or to overuse, said method comprising administering to the patient in need of such preventing or reducing an effective amount of a compound of formula I:

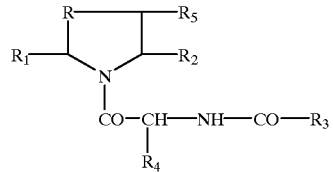

in which

R represents a methylene, ethylene, SO, SO$_2$ or CHOH radical or a sulphur atom, R$_1$ represents a pyridyl radical optionally substituted with one or more identical or different alkyl radicals, a furyl radical optionally substituted with one or more identical or different alkyl radicals, a thienyl radical optionally substituted with one or more identical or different alkyl radicals, a quinolyl radical optionally substituted with one or more identical or different alkyl radicals, a naphthyl radical optionally substituted with one or more identical or different alkyl radicals, an indolyl radical optionally substituted with one or more identical or different alkyl radicals, or a phenyl radical optionally substituted with one or more identical or different substituents chosen from halogen atoms and alkyl, alkoxy, hydroxyl, nitro, amino, monoalkylamino, dialkylamino, alkoxycarbonyl, —CO—NR$_7$R$_8$, —NH—CO—CH$_3$, trifluoromethyl and trifluoromethoxy radicals, and $R_5$ represents a hydrogen atom, or R represents a methylene radical, $R_1$ represents a hydrogen atom and $R_5$ represents a phenyl radical, or R represents a $CHR_6$ radical and $R_1$ and $R_5$ each represent a hydrogen atom;

$R_2$ represents an alkoxycarbonyl, cycloalkyloxycarbonyl, cycloalkylalkyloxycarbonyl or —$CONR_9R_{10}$ radical or a phenyl radical optionally substituted with one or more identical or different substituents chosen from alkyl, alkoxy, and hydroxyl radicals;

$R_3$ represents a phenyl radical optionally substituted with one or more identical or different substituents chosen from halogen atoms and alkyl, alkoxy and alkylthio radicals, or $R_3$ represents a naphthyl, indolyl or quinolyl radical or a phenylamino radical, the phenyl ring of said phenylamino radical being optionally substituted by one or more identical or different substituents chosen from halogen atoms and alkyl, alkoxy, alkylthio, trifluoromethyl, carboxyl, alkoxycarbonyl, hydroxyl, nitro, amino, acyl, cyano, sulphamoyl, carbamoyl, hydroxyiminoalkyl, alkoxyiminoalkyl, hydroxyaminocarbonyl, alkoxyaminocarbonyl, 5-tetrazolyl, 5-tetrazolylalkyl, trifluoromethylsulphonamido, alkylsulphinyl, mono- or polyhydroxyalkyl, sulpho, -alk-O—CO-alk, -alk-COOX, -alk-O-alk, -alk'-COOX, —O-alk-COOX, —CH═CH—COOX and —CO—COOX radicals, or $R_3$ represents an -alk-$SO_3H$ radical in salt form or a —CH═CH-alk', —C(═NOH)—COOX, —S-alk-COOX, —O—$CH_2$-alk'-COOX, —CX═N—O-alk-COOX, -alk-N(OH)—CO-alk, or 2,2-dimethyl-4,6-dioxo-1,3-dioxan-5-yl radical;

$R_4$ represents a hydrogen atom or an alkyl radical;

$R_6$ represents a phenyl radical;

$R_7$ represents a hydrogen atom or an alkyl or phenylalkyl radical or a phenyl radical optionally substituted with one or more identical or different substituents chosen from halogen atoms and alkyl, alkoxy, and alkylthio radicals;

$R_8$ represents an alkyl or phenylalkyl radical or a phenyl radical optionally substituted with one or more identical or different substituents which are halogen atoms, alkyl, alkoxy or alkylthio radicals, or $R_7$ and $R_8$, with the nitrogen atom to which they are attached, form a saturated or unsaturated, mono- or polycyclic heterocycle containing 4 to 9 carbon atoms and one or more identical or different hetero atoms chosen from oxygen and nitrogen, and optionally substituted with one or more identical or different alkyl radicals;

$R_9$ represents a hydrogen atom or an alkyl, cycloalkylalkyl, cycloalkyl or phenylalkyl radical or a phenyl radical optionally substituted with one or more identical or different substituents chosen from halogen atoms and alkyl, alkoxy and alkylthio radicals;

$R_{10}$ represents an alkyl, cycloalkylalkyl, cycloalkyl or phenylalkyl radical or a phenyl radical optionally substituted with one or more identical or different substituents chosen from halogen atoms and alkyl, alkoxy and alkylthio radicals, or $R_9$ and $R_{10}$, together with the nitrogen atom to which they are attached, form a saturated or unsaturated, mono- or polycyclic heterocycle containing 4 to 9 carbon atoms and one or more identical or different hetero atoms chosen from oxygen, nitrogen, and sulfur, and are optionally substituted with one or more identical or different alkyl radicals;

X represents a hydrogen atom or an alkyl or phenylalkyl radical;

alk represents an alkyl or alkylene radical;

alk' represents a hydroxyalkyl, hydroxyalkylene, alkoxyalkyl or alkoxyalkylene radical;

wherein the alkyl, alkylene and alkoxy radicals or portions of radicals contain 1 to 4 carbon atoms in an unbranched or branched chain;

wherein the acyl radicals contain 2 to 4 carbon atoms;

wherein the cycloalkyl radicals contain 3 to 6 carbon atoms; and wherein said drug or substance capable of giving rise to pharmacomania or to overuse is not alcohol;

or a racemate or enantiomer of said compound of Formula I when said compound of Formula I contains one or more asymmetric centers;

or a pharmaceutically acceptable salt of a compound of Formula I, or of a racemate or enantiomer thereof.

2. A method of preventing or reducing self-administration, by a human or animal patient, of a drug or a substance capable of giving rise to pharmacomania or to overuse, as claimed in claim 1, in which R represents a methylene radical, a sulphur atom or an SO radical;

$R_1$ represents an optionally substituted phenyl radical;

$R_2$ represents a phenyl or alkoxycarbonyl radical;

$R_4$ and $R_5$ each independently represent a hydrogen atom; and $R_3$ represents a phenylamino radical in which the phenyl ring is substituted with a carboxyl, -alk-COOH, —S—alk-COOH, hydroxyalkyl, -alk'-COOH or -alk-$SO_3H$ radical.

3. A method of preventing or reducing self-administration, by a human or animal patient, of a drug or a substance capable of giving rise to pharmacomania or to overuse, as claimed in claim 1, in which $R_1$ and $R_2$ are in the cis position with respect to one another.

4. A method of preventing or reducing self-administration, by a human or animal patient, of a drug or a substance capable of giving rise to pharmacomania or to overuse, as claimed in claim 1, in which the compound of formula I is:

tert-butyl (2RS,5SR)-1-{2-[3-(3-((RS)-1-hydroxyethyl)phenyl)ureido]acetyl}-5-phenylprolinate, 2-{3-{3-[2-((2S,5R)-2-tert-butoxycarbonyl-5-phenyl-1-pyrrolidinyl)-2-oxoethyl]ureido}phenyl}propionic acid, (2RS,5SR)-{3-{3-[2-(2-tert-butoxycarbonyl-5-phenyl-1-pyrrolidinyl)-2-oxoethyl]ureido}phenylthio}acetic acid, 2-{3-{3-[2-((2R,4R)-4-tert-butoxycarbonyl-2-(2-fluorophenyl)-3-thiazoldinyl)-2-oxoethyl]ureido}phenyl}propionic acid, potassium (RS)-1-{3-{3-[2-((2R,4R)-4-tert-butoxycarbonyl-2-phenyl-3-thiazolidinyl)-2-oxoethyl]ureido}phenyl}ethanesulphonate, potassium (RS)-1-{3-{3-[2-((2S,5R)-2-tert-butoxycarbonyl-5-phenyl-1-pyrrolidinyl)-2-oxoethyl]ureido}phenyl}ethanesulphonate, potassium (2S,5R)-1-{3-{3-[2-(2-tert-butoxycarbonyl-5-phenyl-1-pyrrolidinyl)-2-oxoethyl]ureido}phenyl}methanesulphonate, (2S,5R)-3-{3-[2-(2-tert-butoxycarbonyl-5-phenyl-1-pyrrolidinyl)-2-oxoethyl]ureido}benzoic acid, (2RS,5SR)-3-{-3-{2-[2-tert-butoxycarbonyl-5-(2-fluorophenyl)-1-pyrrolidinyl]-2-oxoethyl}ureido}benzoic acid, cis-3-{3-[2-(2,5-diphenyl-1-pyrrolidinyl)-2-oxoethyl]
ureido}benzoic acid,
(2RS,5SR)-3-{3-{2-[2-(2-hydroxyphenyl)-5-phenyl-1-
pyrrolidinyl]-2-oxoethyl}ureido}phenylacetic acid,
(2R,4R)-3-{3-[2-(4-tert-butoxycarbonyl-2-phenyl-3-
thiazolidinyl )-2-oxoethyl]ureido}phenylacetic acid,
(2R,4R)-3-{3-[2-(4-tert-butoxycarbonyl-2-phenyl-3-
thiazolidinyl)-2- oxoethyl]ureido}benzoic acid,
2-{3-{3-[2-((1RS,2R,4R)-4-tert-butoxycarbonyl-2-(2-
fluorophenyl)-3-thiazoidinyl-1-oxide)-2-oxoethyl]
ureido}phenyl}propionic acid,
(2R,4R)-3-{3-[2-(4-tert-butoxycarbonyl-2-(2,3-
difuorophenyl)-3-thiazolidinyl)-2-oxoethyl]
ureido}phenylacetic acid, or
tert-butyl (2RS,5SR)-1-{2-{3-[(E)-3-(1-
hydroxyiminoethyl)phenyl]ureido}acetyl}-5-
phenylprolinate;
or a racemate or enantiomer of said compound of Formula I when said compound of Formula I contains one or more asymmetric centers;
or a pharmaceutically acceptable salt of any of the foregoing compounds of Formula I, or of a racemate or enantiomer thereof.

5. A method of preventing or reducing self-administration, by a human or animal patient, of a drug or a substance capable of giving rise to pharmacomania or to overuse, as claimed in claim 1, wherein the drug or substance capable of giving rise to pharmacomania or to overuse is nicotine, caffeine, a benzodiazepine, a narcotic, or a hallucinogen.

6. A method of preventing or reducing self-administration, by a human or animal patient, of a drug or a substance capable of giving rise to pharmacomania or to overuse, as claimed in claim 5, wherein the narcotic is an amphetamine, cocaine, a cannabinoid, morphine, a derivative of morphine, or an opioid.

7. A method of preventing or reducing self-administration, by a human or animal patient, of a drug or a substance capable of giving rise to pharmacomania or to overuse, as claimed in claim 5, wherein the hallucinogen is LSD, ecstasy, mescaline, or psylocibin.

8. A method of preventing or reducing self-administration, by a human or animal patient, of a drug or a substance capable of giving rise to pharmacomania or to overuse, said method comprising administering to the patient in need of such preventing or reducing an effective amount of 2-{3-{3-[2-((2R,4R)-4-tert-butoxycarbonyl-2-(2-fluorophenyl)-3-thiazolidinyl)-2-oxoethyl]ureido}phenyl}propionic acid in racemic form or in enantiomeric form, or a pharmaceutically acceptable salt of any of the foregoing, wherein said drug or substance capable of giving rise to pharmacomania or to overuse is not alcohol.

9. A method of preventing or reducing self-administration, by a human or animal patient, of a drug or a substance capable of giving rise to pharmacomania or to overuse, as claimed in claim 8, wherein said 2-{3-{3-[2-((2R,4R)-4-tert-butoxycarbonyl-2-(2-fluorophenyl)-3-thiazolidinyl)-2-oxoethyl]ureido}phenyl}propionic acid is present in substantially pure enantiomeric excess.

10. A method of preventing or reducing self-administration, by a human or animal patient, of a drug or a substance capable of giving rise to pharmacomania or to overuse, as claimed in claim 8, herein the drug or the substance capable of giving rise to pharmacomania or to overuse is nicotine, caffeine, a benzodiazepine, a narcotic, or a hallucinogen.

11. A method of preventing or reducing self-administration, by a human or animal patient, of a drug or a substance capable of giving rise to pharmacomania or to overuse, as claimed in claim 10, wherein the narcotic is an amphetamine, cocaine, a cannabinoid, morphine, a derivative of morphine, or an opioid.

12. A method of preventing or reducing self-administration, by a human or animal patient, of a drug or a substance capable of giving rise to pharmacomania or to overuse, as claimed in claim 10, wherein the hallucinogen is LSD, ecstasy, mescaline, or psylocibin.

* * * * *

UNITED STATES PATENT AND TRADEMARK OFFICE
CERTIFICATE OF CORRECTION

PATENT NO. : 6,150,387
DATED : November 21, 2000
INVENTOR(S) : Andrees BOHME et al.

It is certified that error appears in the above-identified patent and that said Letters Patent is hereby corrected as shown below:

Claim 4, col. 8, line 52, "thiazoldinyl" should read --thiazolidinyl--.
Claim 4, col. 9, line 10, "thiazoidinyl" should read --thiazolidinyl--.
Claim 4, col. 9, line 13, "difuorophenyl" should read --difluorophenyl--.
Claim 10, col. 10, line 23, "herein" should read --wherein--.

Signed and Sealed this

Eighth Day of May, 2001

*Attest:*

NICHOLAS P. GODICI

*Attesting Officer*     Acting Director of the United States Patent and Trademark Office